United States Patent [19]

Stults

[11] Patent Number: 5,153,335

[45] Date of Patent: Oct. 6, 1992

[54] PROCESS FOR THE PREPARATION OF OXYDIPHTHALIC ANHYDRIDE AND ACYLOXYPHTHALIC ANHYDRIDES

[75] Inventor: Jeffrey S. Stults, Grand Island, N.Y.

[73] Assignee: Occidental Chemical Corporation, Niagara Falls, N.Y.

[21] Appl. No.: 790,839

[22] Filed: Nov. 12, 1991

Related U.S. Application Data

[63] Continuation-in-part of Ser. No. 535,259, Jun. 8, 1990, abandoned.

[51] Int. Cl.$^5$ .......................................... C07D 307/89
[52] U.S. Cl. ........................... 549/243; 549/241
[58] Field of Search ........................ 549/241, 243

[56] References Cited

U.S. PATENT DOCUMENTS

| | | | |
|---|---|---|---|
| 4,697,023 | 9/1987 | Schwartz et al. | 549/241 |
| 4,952,721 | 8/1990 | Fjare | 560/131 |
| 5,003,031 | 3/1991 | Schwartz et al. | 549/241 |
| 5,003,086 | 3/1991 | Stults et al. | 549/241 |

FOREIGN PATENT DOCUMENTS

| | | | |
|---|---|---|---|
| 288974 | 11/1988 | European Pat. Off. | 549/241 |
| 1901028 | 8/1970 | Fed. Rep. of Germany . | |
| 56-74149 | 6/1981 | Japan | 549/241 |
| 7408880 | 1/1976 | Netherlands | 549/241 |

OTHER PUBLICATIONS

Sato et al, Chem. Abst. 113-2128204u (1990).
Von H. Mühlemann, Pharm. Acta. Helv. p. 257 (1948).

*Primary Examiner*—Cecilia Tsang
*Attorney, Agent, or Firm*—Richard D. Fuerle

[57] ABSTRACT

A method for the preparation of acyloxyphthalic anhydride or oxydiphthalic anhydride which comprises the reaction of a halophthalic anhydride with an alkali metal salt and at least a catalytically effective amount of an acid or acid derivative selected from the group consisting of benzoic acids, substituted benzoic acids, benzoic acid salts or substituted benzoic acid salts, and hydrolyzable benzoyl esters, and hydrolyzable substituted benzoyl esters, alkyl carboxylic acids, hydrolyzable esters of alkyl carboxylic acids, and salts of alkyl carboxylic acids. The process may be conducted without solvent, in a polar solvent or in a non-polar solvent using a phase transfer catalyst.

52 Claims, No Drawings

PROCESS FOR THE PREPARATION OF OXYDIPHTHALIC ANHYDRIDE AND ACYLOXYPHTHALIC ANHYDRIDES

This application is a continuation-in-part of application Ser. No. 07/535,259, filed Jun. 8, 1990, and now abandoned.

BACKGROUND OF THE INVENTION

This invention relates to a process for the preparation of acyloxyphthalic anhydrides and oxydiphthalic anhydride from halophthalic anhydrides. More particularly, this invention relates to the use of benzoic acids, substituted benzoic acids, benzoic acid salts, substituted benzoic acid salts, benzoyloxyphthalic anhydrides, and substituted benzoyloxyphthalic anhydrides as catalysts for the reactions of a halophthalic anhydride to yield the compounds noted above.

Acyloxyphthalic anhydrides are particularly useful in the synthesis of oxydiphthalic anhydrides. By known methods the acyloxyphthalic anhydrides can be hydrolyzed to yield hydroxyphthalic anhydrides. The hydroxyphthalic anhydrides can be used to prepare oxydiphthalic anhydrides (U.S. Pat. No. 4,837,404). The acyloxyphthalic anhydrides are also useful as curing agents for epoxy resins. The other product of this invention, oxydiphthalic anhydride, is useful as a monomer for the preparation of polyimide resins. Polyimides can be produced by reacting an oxydiphthalic anhydride with a suitable diamine and dehydrating the resulting polyamic acid. Polyimide resins are particularly useful in electrical and high temperature applications.

Oxydiphthalic anhydride has been prepared by several methods. U.S. Pat. No. 4,697,023, incorporated herein by reference, discloses that a halophthalic anhydride, water, and an alkali metal compound such as potassium fluoride or potassium carbonate will react, in the presence of a dipolar aprotic solvent, to form oxydiphthalic anhydride.

U.S. Pat. No. 4,837,404 teaches that oxydiphthalic anhydride can be prepared by reacting a halophthalic anhydride with an hydroxyphthalic anhydride in a polar aprotic solvent in the presence of an alkali metal compound such KF, CsF, or $K_2CO_3$.

U.S. Pat. No. 4,808,731 teaches a method of preparing oxydiphthalic anhydride by reacting a substituted phthalic anhydride such as 4-nitro or 4-fluorophthalic anhydride with a dialkyl aminopyridine in the presence of a refluxing, non-polar organic solvent.

U.S. Pat. No. 4,558,164 discloses a process for preparing a symmetrical dinitrodiphenyl ether from o- or p-nitrochlorobenzene or o- or p-nitrofluorobenzene comprising using a polar organic solvent, a potassium salt of a fatty carboxylic acid containing 2 to 20 carbon atoms or a potassium salt of an aromatic carboxylic acid containing 7 to 12 carbon atoms as catalyst, and either sodium or potassium carbonate to react with the p-nitrochlorobenzene. The reaction is carried out at from 150° to 210° C. until the o- or p-nitrochlorobenzene or o- or p-nitrofluorobenzene reacts. The method of U.S. Pat. No. 4,558,164 (Example 5) was tested using 4-chlorophthalic anhydride as a starting material. No oxydiphthalic anhydride was produced. (see Comparative Examples 3 and 4)

U.S. Pat. No. 4,780,544 teaches a method of preparing oxy-di(N-alkyl or aryl) phthalimides. In this process nitro-N-alkyl or aryl phthalimide is treated with an alkali metal carboxylate salt. Sodium, potassium, and cesium salts of acetic acid, propionic acid and benzoic acid are disclosed as suitable carboxylate salts and the effective amount is 0.25 to 1 mole of carboxylate per mole of nitrophthalimide.

Muehlemann (Pharm. Acta Helv. 23; 1948 p. 257) discloses the preparation 3-acetoxyphthalic acid from 3-hydroxyphthalic acid and acetic anhydride. Similarly, Japanese Patent application 85-238,404 as abstracted in CA 107 (22):199080 g, discloses that 4-hydroxyphthalic anhydride biesters can be prepared by the condensation of 4-hydroxyphthalic anhydride with diacid chlorides. The biesters are formed from the di-acid chloride and the hydroxy portion of the hydroxyphthalic anhydride. The anhydride portion of the molecule remains intact. German Patent DE1901028 (August, 1970), discloses that terephthalate esters of hydroxyphthalic anhydride can be prepared by the transesterification of 4-acetoxyphthalic anhydride with terephthalic acid in the presence of magnesium.

SUMMARY OF THE INVENTION

A method for the preparation of acyloxyphthalic anhydride or oxydiphthalic anhydride which comprises the reaction of a halophthalic anhydride with an alkali metal salt and at least a catalytically effective amount of an carboxylic acid or acid derivative including benzoic acid, substituted benzoic acids, benzoic acid salts or substituted benzoic acid salts, and hydrolyzable benzoyl esters, and hydrolyzable substituted benzoyl esters, alkyl carboxylic acids, hydrolyzable esters of alkyl carboxylic acids, and salts of alkyl carboxylic acids. The process can be conducted without solvent, in a polar solvent or in a non-polar solvent using a phase transfer catalyst.

DETAILED DESCRIPTION OF THE INVENTION

The present invention relates to the reaction of halophthalic anhydrides with alkali metal salts, in a non-aqueous medium to form acyloxyphthalic anhydrides, or oxydiphthalic anhydride. The preferred alkali metal salts are potassium carbonate, potassium fluoride, cesium fluoride, or sodium carbonate.

In the absence of a catalyst, the reaction of halophthalic anhydride with an alkali metal salt, such as potassium carbonate, is slow. Comparative examples 1 and 2 illustrated such reactions. Surprisingly, it has now been found that small catalytic quantities of a carboxylic acid or acid derivative catalyze the reaction between a halophthalic anhydride and an alkali metal salt in a non-aqueous medium. The preferred acid or acid derivatives are benzoic acid, substituted benzoic acids, benzoic acid salts, substituted benzoic acid salts, hydrolyzable benzoyl esters, and hydrolyzable substituted benzoyl esters, alkyl carboxylic acids, hydrolyzable esters of alkyl carboxylic acids, and salts of alkyl carboxylic acids. Hereinafter, the term acid or acid derivatives means a carboxylic acid or derivatives thereof, benzoic acid, substituted benzoic acids, benzoic acid salts, substituted benzoic acid salts, hydrolyzable benzoyl esters including esters of benzoic acids and substituted benzoic acids, alkyl carboxylic acids, hydrolyzable esters of alkyl carboxylic acids, or salts of alkyl carboxylic acids. The term alkyl carboxylic acids includes $C_2$ to $C_{12}$ straight, branched chain, and cyclic acids. Most esters of benzoic acids, or alkyl carboxylic acids, are hydrolyzable under the conditions of this reaction. However, esters with steric hindrance near the carboxyl group, or other unusual structural features may not hydrolyze readily enough to be useable as catalysts for the reaction. Those skilled in the art will appreciate which esters are suitable as catalysts. Benzoyloxyphthalic anhydride or a substituted benzoyloxyphthalic anhydrides such as 4-(chlorobenzoyloxy)phthalic anhydride, and simple esters such as ethyl acetate, and ethyl benzoate are suitable catalysts for use in the present invention. The selected catalyst should not contain substituents that interfere with the reaction of this invention. In addition, if a low boiling ester or alkyl carboxylic acid is selected as the catalyst, steps must be taken to prevent its loss during the course of the reaction. A wide variety of benzoate salts and alkyl carboxylate salts are suitable for use as catalysts. However, the Li, Na, K, Cs and $NH_4+$ salts are preferred. A wide variety of substituted benzoic acids are catalytically effective. However, the preferred substituents are nitro, halo, dihalo, trihalo, cyano and trihalomethyl. The preferred alkyl carboxylic acids are the $C_2$ to $C_6$ alkyl carboxylic acids including branched chain and cyclic isomers.

A non-aqueous medium means either a non-aqueous solvent, or no solvent. If no solvent is used, the halophthalic anhydride itself acts as the solvent. The effective quantity of the catalyst is less than about 1 mole percent based upon the quantity of halophthalic anhydride.

The reaction of a halophthalic anhydride with an alkali metal salt, in the presence of the acid or acid derivative, produces two products, acylocyphthalic anhydrides, and oxydiphthalic anhydride:

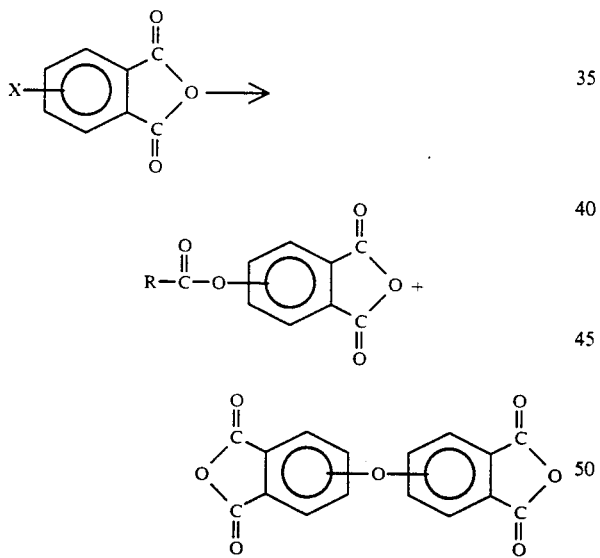

where x=F, Cl, Br, or I and R is phenyl, substituted phenyl, and C2 to C12 alkyl.

As set forth more fully below, the reaction conditions can be varied to emphasize one product at the expense of the other. For example, the catalyst can take two different roles in the reaction of this invention. If the selected catalyst is present in small quantities, it acts predominantly as a catalyst for the reaction, and the reaction produces mainly oxydiphthalic anhydride. However, traces of acyloxyphthalic anhydride may be present. On the other hand, if the concentration of the catalyst is higher, the catalyst becomes a reactant as well, and an acyloxyphthalic anhydride is an observed product. If the catalyst is present in large enough concentrations to act as a reactant, low temperature reactions tend to favor the production of acyloxyphthalic anhydrides. Higher temperatures favor the formation of oxydiphthalic anhydride.

The process of this invention applies to a wide variety of halophthalic anhydrides. The halogen substituent on the starting halophthalic anhydride can be fluorine, chlorine, bromine or iodine. The preferred halo substituents are fluorine and chlorine. Both the 3-halo and 4-halo phthalic anhydride can be used in this reaction. Accordingly, it is possible, using the method of this invention, to prepare 3-acyloxyphthalic anhydrides, 4-acyloxyphthalic anhydrides, 3,3'-oxydiphthalic anhydride, 4,4'-oxydiphthalic anhydride and 3,4'-oxydiphthalic anhydride.

The reaction can be conducted without solvent, or in a wide variety of solvents. If the reaction is run without a solvent, care must be taken to avoid overheating, which can cause color forming side reactions. If the reaction is run in a solvent, it is preferable to use solutions of high concentration. Typical concentrations are 1:1 by weight. The reaction can be conducted in more dilute solutions. However, the rate of the reaction may be slower in such solutions, and the solvent removal on workup may be more difficult. Solvents containing a reactive group such as an hydroxyl or a primary or secondary amine are not suitable. Polar, aprotic solvents such as dimethyl sulfoxide, sulfolane, dimethylsulfone, N,N-dimethyl formamide (DMF), hexamethylphosphoramide, N-methyl pyrrolidone, and dimethyl acetamide are suitable for this process. Less polar solvents of a moderately high boiling point, such as bromobenzene, chlorobenzene, dichlorobenzenes, trichlorobenzenes, benzonitrile, dichlorotoluenes, and chloroxylenes can also be used. The preferred solvent is 1,2,4-trichlorobenzene. Less polar solvents of lower boiling point, such as toluene, can be used, provided that the reaction is conducted under sufficient pressure to achieve the desired temperature. In polar solvents, the reactants are sufficiently soluble and a phase transfer catalyst is not required. In less polar solvents, it is preferable to use phase transfer catalysts to increase the rate of the reaction.

Phase transfer catalysts combine, within the same molecule, both polar and non-polar regions. The non-polar regions of the phase transfer catalyst allow it to dissolve in non-polar solvents. On the other hand, the polar regions of the molecule allow for interaction with more polar species. Accordingly, a phase transfer catalyst can affect the solubility of a polar species in a non-polar solvent. In the absence of a catalyst, a polar species, such as a benzoate ion, might be rather insoluble in a non-polar solvent. In the presence of a phase transfer catalyst, the ion can exist in a non-polar solvent in appreciable concentrations. A wide variety of phase transfer catalysts will allow this process to function in non-polar solvents. Among the phase transfer catalysts that are useful in this invention are tetraalkyl ammonium salts, N-alkyl pyridinium salts, tetraalkyl phosphonium salts, crown ethers, polyethers, and tetraphenyl phosphonium salts. The choice of phase transfer catalysts depends on the temperature at which the reaction is to be conducted. For example, if the reaction can be conducted at 150° C. or less, tetra alkyl ammonium salts are useable. On the other hand, at higher temperatures more stable catalysts such as tetraphenyl phosphonium salts are preferred. The most preferred phase transfer catalysts are tetraphenyl phosphonium benzoates, tetraphenyl phosphonium substituted benzoates, and tetraphenyl phosphonium halides. Among the substituted benzoates which may be used in such catalysts are nitrobenzoates, halobenzoates, alkylbenzoates, and alkoxybenzoates.

The temperature at which the reaction is conducted depends upon the halophthalic anhydride chosen as a starting material. If a fluorophthalic anhydride is selected as the starting material, the reaction may be run between about 120° and 250° C. Chlorophthalic anhydride requires a reaction temperature of about 170° to 275° C. Bromophthalic anhydrides fall between fluoro and chlorophthalic anhydrides in temperature requirements.

The time of reaction is highly dependent both upon the temperature, and upon the concentration of solution. As with most chemical reactions, the reaction is over more quickly at higher temperatures; however, side reactions become more available at the higher temperatures. Similarly, the reaction is rapid in solutions of high concentrations. However, reactions run in more concentrated solutions may suffer from side reactions. The reaction can be run at a concentration of 2 parts solvent to one part halophthalic anhydride starting material or lower concentrations of the halophthalic anhydride. In selecting appropriate conditions, one must balance speed of reaction and purity of the final product.

The reaction can be run to completion. However, it is often found that when the reaction is run to completion, colored side products are formed. Accordingly, it is often desirable to limit the amount of basic salt used in the reaction, and to limit the reaction time so that the reaction goes only part way to completion. Fractional crystallization will readily separate the reaction product oxydiphthalic anhydride from the halophthalic anhydride starting material which can be readily recovered and recycled. Depending upon the source, the halophthalic anhydride starting material may contain impurities that inhibit the reaction. Although the nature of these impurities is not entirely certain, their effect can be controlled by heating the halophthalic anhydride with the basic salt prior to the addition of the catalyst.

The kinetics of this reaction are rather complex. The role of the catalyst is not simple. The carboxylic acid, alkyl carboxylic acid or benzoic acid derivative that produces the best results, as a catalyst, varies depending upon the reaction conditions. It has been observed that in non-polar solvents, the more acidic derivatives of benzoic acid, such as nitrobenzoic acid, dinitrobenzoic acid, halobenzoic acids, dihalobenzoic acids, trihalobenzoic acids, cyanobenzoic acids and trihalomethyl benzoic acids and the more acidic alkyl carboxylic acids tend to be more effective as catalysts. On the other hand, benzoic acid, alkylbenzoic acids, alkoxybenzoic acids, or their salts as well as the less acid alkyl carboxylic acids are very effective catalysts in more polar solvents. In the preferred solvent, 1,2,4-trichlorobenzene, monohalobenzoic acids are the preferred catalysts. For any given solvent, the preferred catalyst can easily be determined by conducting two or three small scale experiments with catalysts of different acidity.

The role of water in the reaction is unusual. If an alkali metal carbonate is used as the basic salt, water is produced during the reaction when the basic salt scavenges the acid produced by the displacement of the halogen from the halophthalic anhydride. Some water is necessary for the reaction to begin. However, excessive amounts of water are undesirable because water can react with the phthalic anhydride to form phthalic acid. This reaction reduces the yield of the desired product. In addition, there are other side reactions caused by water that can lead to gel formation, and a disastrous loss of yield. In fact, the effect of excess water is far greater than that which would be expected by substituting the amount of reagent sidetracked by water from the overall yield. It has been found that when the basic salt is potassium carbonate, and reaction is run in a solvent, it is preferable that the solvent contain approximately 0.05 to 0.5 mole % total water based upon the halophthalic anhydride in order for the reaction to proceed appropriately. On the other hand, it has been found that if the total water in the solvent is 0.5 mole % or above, based upon the halophthalic anhydride, the yield of product is decreased.

In a typical example, such as Example 2, a solvent water content of 0.05 mole % based upon the halophthalic anhydride would correspond to 48 ppm water in the solvent. Similarly, 0.2 mole % water would correspond to 192 ppm while 0.5 mole % would correspond to 480 ppm. In addition, there are other sources of solvent which must be considered. When an alkali metal carbonate salt is used as the base, it is a major source of water. Alkali metal carbonates generally contain several percent water and we have found that, unless one is dealing with a particularly dry source of carbonate, it is preferable that they be dried before being used in the reaction. Even oven-dried alkali metal carbonate salts appear to contain some water, although precise quantitation of this water is often difficult. Another unanticipated source of water is phthalic acid derivatives which may be present as impurities in the phthalic anhydride starting material. Each mole of the acid reacts with one mole of carbonate to form one mole of water. In a typical example, such as Example 2, half a mole percent of chlorophthalic acid in the chlorophthalic anhydride starting material corresponds to approximately 480 ppm extra water in the solvent, or 235 ppm extra water overall (counting the weight of all solvents and reactants). We have found that control of water is extremely important in conducting this reaction in the presence of carbonate salts, and that the overall level of water, counting water from all sources, and considering the weight of all ingredients present in the reaction mixture, should be less than approximately 2000 ppm. In addition, we have found that in laboratory scale experiments it is possible to create a reaction mixture which contains too little water to function effectively. We believe that the reaction requires an initial total water level of above approximately 100 ppm. While this lower limit may be of interest when the process is conducted as a laboratory scale reaction, on an industrial scale, lack of water has not been found to be a problem. Even with good technique, residual moisture on the surface of the reactor, residual moisture remaining in the carbonate, moisture contained in the solvents, as well as the traces of chlorophthalic acid in the starting material, provide sufficient water. If the reaction is run under exceptional circumstances such that there is insufficient water present, those skilled in the art will have little difficulty in determining how much water to add in order to allow the reaction to proceed.

When alkali metal carbonate salts are used as the base, it is preferable to conduct the reaction in a substantially anhydrous reaction medium. As used herein, the term "substantially anhydrous," shall mean containing greater than approximately 100 ppm and less than approximately 2000 ppm water based on the total weight of all ingredients in the reaction mixture. Thus, a substantially anhydrous reaction mixture is one containing more than approximately 100 ppm water, and less than approximately 2000 ppm. Techniques have been developed for controlling the amount of water in the reaction mixture. Alkali metal carbonates can be heated to a temperature of approximately 200° C. prior to being used in the reaction. This treatment will drive off a substantial portion, although probably not all, of the water contained in the carbonate salt. If it is suspected that the halophthalic anhydride used in the reaction contains impurities of a halophthlaic acid, the anhydride can be heated to cause further cyclization, or the anhydride can be mixed with a high boiling water immiscible solvent and refluxed with a small amount of carbonate. This treatment will cause cyclization of the acid to the anhydride, through heat, and, in addition, the small amount of carbonate present will react with the acid to form the carboxylate salt, water and carbon dioxide. The water from the cyclization and the water from the reaction with the carbonate can be removed from the system by condensing the high boiling solvent at a temperature fairly close to the boiling point of water. The high boiling solvent condenses while the water vapor is lost. Solvents can be dried by methods well-known to those skilled in the art.

When potassium fluoride or cesium fluoride is used as the basic salt, the role of water is somewhat different. Here water is not produced during the reaction, and some water must be provided in order for the reaction to occur. Depending upon which product is desired, one can readily calculate how much water is required. For example, if the desired product is the acyloxyphthalic anhydride, no additional water is required. However, if the desired product is the oxydiphthalic anhydride, one half mole of water is required for each mole of halophthalic anhydride starting material. If sufficient water is not present in the solvent or in the reactants, it may be necessary to add some water to the reaction mixture in order to obtain the desired product.

The process of the present invention provides a novel route to the synthesis of a wide variety of acyloxyphthalic anhydrides. Among the novel compounds that can be produced by the process of the invention are acyloxyphthalic anhydrides of the formulas

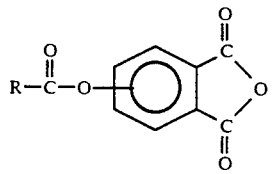

where R is selected from the group consisting of $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, and $C_{11}H_{23}$, including branched isomers of those formulas and cyclic saturated hydrocarbon radicals containing 3 to 11 carbon atoms; and

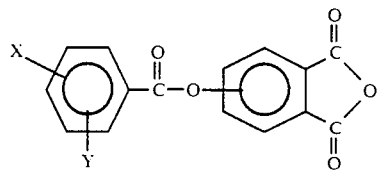

where X and Y are substituents independently selected from the group consisting of H, F, Cl, Br, $NO_2$, $CH_3$, $CF_3$, $CCl_3$ and CN, provided that X and Y can not both be H.

The role of water in the production of acyloxyphthalic anhydrides is different from its role in the production of oxydiphthalic anhydride. Water is not a reactant in the production of acyloxyphthalic anhydride whereas it is in the production of oxydiphthalic anhydride. Accordingly, in order to maximize the amount of acyloxyphthalic anhydrides produced, the amount of water should be minimized. The presence of any substantial quantity of water will result in the formation of oxydiphthalic anhydride at the expense of the acyloxyphthalic anhydride. If rigorous exclusion of water is not feasible, the process can be run to produce acyloxyphthalic anhydrides. However, some oxydiphthalic anhydride will be produced, and the desired acyloxyphthalic anhydride will have to be separated from the oxydiphthalic anhydride. This separation can be accomplished by recrystallization, or other methods well known to those skilled in the art.

Without further elaboration, it is believed that one skilled in the art can, using the preceding description, utilize the present invention to its fullest extent. The following specific embodiments are, therefore, to be construed as merely illustrative, and not limiting, in any way, the remainder of the disclosure. In the following examples, all temperatures are set forth uncorrected in degrees Celsius and parts and percentages are by weight, unless otherwise indicated.

The present invention is further illustrated by the examples given below. However, it is to be understood that the present invention is not limited by these specific examples. In the examples all carbonate salts were dried in an oven at 180° C. for several hours before being used in the reaction unless otherwise stated

EXAMPLE 1

4-Chlorophthalic anhydride (30 g, 160 mmol) and benzonitrile (Aldrich, 30 g, containing 110 ppm water) were heated to reflux. Dry potassium carbonate (1.2 g, 8.7 mmol) was added and the mixture heated for 30 minutes. Tetraphenyl phosphonium bromide (0.36 g, 0.9 mmol) and 4-chlorobenzoic acid (0.06 g, 0.4 mmol) were added followed by addition of potassium carbonate (11.4 g, 82.2 mmol). The reaction was heated for about 9 hours and then was diluted with benzonitrile (30 g) and filtered. The 4,4'-oxydiphthalic anhydride was allowed to crystallize, was washed with solvent, and dried in an air circulating oven at 120° C. to give crude 4,4'-oxydiphthalic anhydride, 24.7 g.

EXAMPLE 2

4-Chlorophthalic anhydride (30 g, 1 60 mmol) and 1,2-dichlorobenzene (Aldrich, 30 g) were heated to reflux. Dry potassium carbonate (1.04 g, 7.5 mmol) was added and the mixture heated for 30 minutes. Tetraphenyl phosphonium bromide (0.36 g, 0.9 mmol) and 4- chlorobenzoic acid (0.06 g, 0.4 mmol) were added followed by addition of potassium carbonate (11.4 g, 82.2 mmol). The reaction was heated for about 10 hours and then was diluted with 1,2-dichlorobenzene (60 g) and filtered. The 4,4'-oxydiphthalic anhydride was allowed to crystallize, was washed with solvent, and dried in an air circulating oven at 120° C. to give crude 4,4'-oxydiphthalic anhydride, 22.3 g.

EXAMPLE 3

4-Chlorophthalic anhydride (30 g, 160 mmol) and 2,4-dichlorotoluene (Aldrich, 30 g) were heated to reflux at approximately 218° C. Dry potassium carbonate (1.32 g, 12 mmol) was added and the mixture heated for about 30 minutes. Tetraphenyl phosphonium bromide (0.36 g, 0.9 mmol) and 4-chlorobenzoic acid (0.06 g, 0.4 mmol) were added followed by addition of potassium carbonate (11.4 g, 82.2 mmol) over 45 minutes. The reaction was heated for about 6 hours and then was diluted with 2,4-dichlorotoluene (60 g) and filtered. The 4,4'-oxydiphthalic anhydride was allowed to crystallize, was washed with solvent, and dried in an air circulating oven at 120° C. to give crude 4,4'-oxydiphthalic anhydride, 20.3 g.

EXAMPLE 4

4-Chlorophthalic anhydride (30 g, 160 mmol) and 2,6-dichlorotoluene (Aldrich, 15 g) were heated to reflux at approximately 221° C. Dry potassium carbonate (1.26 g, 9.1 mmol) was added and the mixture heated for about 1 hour. Tetraphenyl phosphonium bromide (0.36 g, 0.9 mmol) and 4-chlorobenzoic acid (0.06 g, 0.4 mmol) were added followed by addition of potassium carbonate (11.4 g, 82.2 mmol). The reaction was heated for about 6.5 hours and then was diluted with 2,6-dichlorotoluene (60 g) and filtered. The 4,4'-oxydiphthalic anhydride was allowed to crystallize, was washed with solvent, and dried in an air circulating oven at 120° C. to give crude 4,4°-oxydiphthalic anhydride, 23 g.

EXAMPLE 5

4-Chlorophthalic anhydride (30 g, 160 mmol) and 2,5-dichlorotoluene (Aldrich, 15 g) were heated to reflux at approximately 230° C. Dry potassium carbonate (1.26 g, 9.1 mmol) was added and the mixture heated for about 1 hour. Tetraphenyl phosphonium bromide (0.36 g, 0.9 mmol) and 4-chlorobenzoic acid (0.06 g, 0.4 mmol) were added followed by addition of potassium carbonate (11.4 g, 82.2 mmol). The reaction was heated for about 5 hours and then was diluted with 2,5-dichlorotoluene (60 g) and filtered. The 4,4°-oxydiphthalic anhydride was allowed to crystallize, was washed with solvent, and dried in an air circulating oven at 120° C. to give crude 4,4'-oxydiphthalic anhydride, 20.9 g.

EXAMPLE 6

4-Chlorophthalic anhydride (30 g, 160 mmol) and mixed dichlorotoluenes (15 g) were heated to reflux. Dry potassium carbonate (1.29 g, 9.3 mmol) was added and the mixture heated for about 1 hour. Tetraphenyl phosphonium bromide (0.36 g, 0.9 mmol) and 4-chlorobenzoic acid (0.06 g, 0.4 mmol) were added followed by addition of potassium carbonate (11.4 g, 82.2 mmol). The reaction was heated for about 10 hours and then was diluted with mixed dichlorotouluenes (60 g) and filtered. The 4,4'-oxydiphthalic anhydride was allowed to crystallize, was washed with solvent, and dried in an air circulating oven at 120° C. to give crude 4,4'-oxydiphthalic anhydride, 18.4 g.

EXAMPLE 7

3-Chlorophthalic anhydride (30.1 g, 160 mmol) and 1,2,4-trichlorobenzene (30.5 g) were heated to reflux. Dry potassium carbonate (1.17 g, 8.5 mmol) was added and the suspension heated for 1 hour. Tetraphenyl phosphonium bromide (0.36 g, 0.9 mmol) and 4-chlorobenzoic acid (0.06 g, 0.4 mmol) was added followed by addition of more potassium carbonate (11.36 g, 82.2 mmol). The reaction was heated for approximately 12 hours. The reaction mixture was diluted with 1,2,4-trichlorobenzene (60 ml), filtered, and 3,3'-oxydiphthalic anhydride allowed to crystallize. The solid was collected, washed with solvent, and dried in an air circulating oven at 120° C. to give crude 3,3'-oxydiphthalic anhydride, 19.6 g.

EXAMPLE 8

4-Chlorophthalic anhydride (10 g, 55 mmol), potassium benzoate (1.0 g, 6.2 mmol), and sulfolane (25 g) were heated to about 162° C. Potassium carbonate (3.87 g, 28 mmol) was added and the suspension was heated to about 175° C. After 4 hours, gas chromatography (GC) analysis indicated a 6:3 ratio of 4,4'-oxydiphthalic anhydride to 4-chlorophthalic anhydride.

EXAMPLE 9

4-Chlorophthalic anhydride (10 g, 55 mmol), potassium benzoate (1.0 g, 6.2 mmol), and N,N-dimethylformamide (25 g) were heated to reflux. Potassium carbonate (3.87 g, 28 mmol) was added. After about 6.5 hours, GC analysis indicated a 2:1 ratio of 4,4'-oxydiphthalic anhydride to 4-chlorophthalic anhydride.

EXAMPLE 10

4-Chlorophthalic anhydride (10 g, 55 mmol), potassium benzoate (1.0 g, 6.2 mmol), and N-methylpyrrolidinone (25 g) were heated to about 175.C. Potassium carbonate (3.87 g, 28 mmol) was added and the suspension was heated to about 175.C. After 2 hours, GC analysis indicated a greater than 97% conversion to 4,4'-oxydiphthalic anhydride. The solvent was removed under reduced pressure and the residue treated with an aqueous 25% sodium hydroxide solution. The solution was acidified with concentrated HCl. The solid was collected and dried to give 4,4'-oxydiphthalic acid (4.85 g) mixed with some sodium chloride. The tetra acid was cyclized and recrystallized from hot acetic anhydride (2.4 mL) and filtered to remove salts to give 4,4'-oxydiphthalic anhydride, 4.2 g.

EXAMPLE 11

4-Chlorophthalic anhydride (30 g, 160 mmol), and nitrobenzene (Aldrich, 30 g, containing 500 ppm water) were heated to reflux. Dry potassium carbonate (1.32 g, 9.6 mmol) was added and the mixture heated for 30 minutes. Tetraphenyl phosphonium bromide (0.36 g, 0.9 mmol) and 4-chlorobenzoic acid (0.06 g, 0.4 mmol) were added followed by addition of potassium carbonate (11.4 g, 82.2 mmol). The reaction was heated for about 9 hours and then was diluted with nitrobenzene (30 g) and filtered. The 4,4'-oxydiphthalic anhydride was allowed to crystallize, was washed with solvent, and dried in an air circulating oven at 120° C. to give crude 4,4'-oxydiphthalic anhydride, 10.0 g.

EXAMPLE 12

4-Chlorophthalic anhydride (30 g, 160 mmol) and 1,2,4-trichlorobenzene (30 g) were heated to reflux (approximately 224° C.) and tetraphenyl phosphonium bromide (Hokko Chemical, 0.30 g, 0.7 mmol) and 4-chlorobenzoic acid (Aldrich, 0.06 g, 0.4 mmol) were added. Dry potassium carbonate (7.95 g, 58 mmol) was then added in portions over one hour. The reaction was monitored by GC and showed 62.9% conversion to 4,4'-oxydiphthalic anhydride (ODPAN) 3 hours after addition of carbonate was completed. The reaction was heated for 3.5 hours after addition of potassium carbonate and was then diluted with 1,2,4-trichlorobenzene (60 g), filtered, and the ODPAN allowed to recrystallize. The ODPAN was collected and washed with 1,2,4-trichlorobenzene followed by hexanes and dried in an air circulating oven at 120° C. to give crude ODPAN, 16.4 g (100% based on conversion of 4-chlorophthalic anhydride).

EXAMPLE 13

4-Chlorophthalic anhydride (30 g, 160 mmol) and 1,2,4-trichlorobenzene (30 g) were heated to reflux (approximately 224° C.) and tetraphenyl phosphonium bromide (Hokko Chemical, 0.30 g, 0.7 mmol) and 3-bromobenzoic acid (Aldrich, 0.06 g, 0.4 mmol) were added. Dry potassium carbonate (7.95 g, 58 mmol) was then added in portions over one hour. The reaction was monitored by GC and showed 61.2% conversion to 4,4'-oxydiphthalic anhydride (ODPAN) 3 hours after addition of carbonate was completed. The reaction was heated for 3.5 hours after addition of potassium carbonate and was then diluted with 1,2,4-trichlorobenzene (60 g), filtered, and the ODPAN allowed to recrystallize. The ODPAN was collected and washed with 1,2,4-trichlorobenzene followed by hexanes and dried in an air circulating oven at 120° C. to give crude ODPAN, 16.4 g (100% based on conversion of 4-chlorophthalic anhydride).

EXAMPLE 14

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 3,4-dichlorobenzoic acid (Aldrich, 0.06 g, 0.4 mmol) were added. Dry potassium carbonate (7.95 g, 58 mmol) was then added in portions over one hour. The reaction was monitored by GC and showed 48% conversion to 4,4'-oxydiphthalic anhydride (ODPAN) 3.5 hours after addition of carbonate was completed. The reaction was heated for 6 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 13.8 g (89% based on conversion of 4-chlorophthalic anhydride).

EXAMPLE 15

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 2,4-dichlorobenzoic acid (Aldrich, 0.09 g, 0.4 mmol) were added. Dry potassium carbonate (7.95 g, 58 mmol) was then added in portions over one hour. The reaction was monitored by GC and showed 47.2% conversion to 4,4'-oxydiphthalic anhydride (ODPAN) 4 hours after addition of carbonate was completed. The reaction was heated for 7 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 12.96 g (100% based on conversion of 4-chlorophthalic anhydride).

EXAMPLE 16

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 2-chlorobenzoic acid (Aldrich, 0.06 g, 0.4 mmol) were added. Dry potassium carbonate (7.95 g, 58 mmol) was then added in portions over one hour. The reaction was monitored by GC and showed 14.9% conversion to 4,4'-oxydiphthalic anhydride (ODPAN) 4 hours after addition of carbonate was completed.

EXAMPLE 17

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 4-bromobenzoic acid (Aldrich, 0.09 g, 0.4 mmol) were added. Dry potassium carbonate (7.95 g, 58 mmol) was then added in portions over one hour. The reaction was monitored by GC and showed 49.6% conversion to 4,4'-oxydiphthalic anhydride (ODPAN) 3 hours after addition of carbonate was completed. The reaction was heated for 3.5 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 14.7 g (100% based on conversion of 4-chlorophthalic anhydride).

EXAMPLE 18

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 3,5-dichlorobenzoic acid (Aldrich, 0.09 g, 0.4 mmol) were added. Dry potassium carbonate (7.95 g, 58 mmol) was then added in portions over one hour. The reaction was monitored by GC and showed 31.9% conversion to 4,4'-oxydiphthalic anhydride (ODPAN) 3 hours after addition of carbonate was completed. The reaction was heated for 7 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 12.8 g (100% based on conversion of 4-chlorophthalic anhydride).

EXAMPLE 19

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 3-chlorobenzoic acid (Aldrich, 0.06 g, 0.4 mmol) were added. Dry potassium carbonate (7.95 g, 58 mmol) was then added in portions over one hour. The reaction was monitored by GC and showed 26.7% conversion to 4,4'-oxydiphthalic anhydride (ODPAN) 4 hours after addition of carbonate was completed. The reaction was heated for 11.5 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 10.22 g (100% based on conversion of 4-chlorophthalic anhydride).

EXAMPLE 20

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 4-methoxybenzoic acid (Aldrich, 0.06 g, 0.4 mmol) were added. Dry potassium carbonate (7.95 g, 58 mmol) was then added in portions over one hour. The reaction was monitored by GC and showed 3.7% conversion to 4,4'-oxydiphthalic anhydride (ODPAN) 4 hours after addition of carbonate was completed.

EXAMPLE 21

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 4-methylbenzoic acid (Aldrich, 0.05 g, 0.4 mmol) were added. Dry potassium carbonate (7.95 g, 58 mmol) was then added in portions over one hour. The reaction was monitored by GC and showed 3.7% conversion to 4,4'-oxydiphthalic anhydride (ODPAN) 4 hours after addition of carbonate was completed.

EXAMPLE 22

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 3-nitrobenzoic acid (Aldrich, 0.07 g, 0.4 mmol) were added. Dry potassium carbonate (7.95 g, 58 mmol) was then added in portions over one hour. The reaction was monitored by GC and showed 12.5% conversion to 4,4'-oxydiphthalic anhydride (ODPAN) 4 hours after addition of carbonate was completed. The reaction was heated for 11.5 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 4.52 g (100% based on conversion of 4-chlorophthalic anhydride).

EXAMPLE 23

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) and 4-nitrobenzoic acid (Aldrich, 0.07 g, 0.4 mmol) were added. Dry potassium carbonate (7.95 g, 58 mmol) was then added in portions over one hour. The reaction was monitored by GC and showed 23.1% conversion to 4,4'-oxydiphthalic anhydride (ODPAN) 4 hours after addition of carbonate was completed. The reaction was heated for 11.5 hours after addition of potassium carbonate and was then diluted with 1,2,4-trichlorobenzene (30 g), filtered, and the ODPAN allowed to recrystallize. The ODPAN was collected and washed with 1,2,4-trichlorobenzene followed by hexanes and dried in an air circulating oven at 120° C. to give crude ODPAN, 9.49 g (100% based on conversion of 4-chlorophthalic anhydride).

EXAMPLE 24

4-Chlorophthalic anhydride (30 g, 160 mmol), tetraphenyl phosphonium bromide (0.3 g, 0.7 mmol), and 4-chlorobenzoic acid (0.06 g, 0.4 mmol) were heated to approximately 220° C. Potassium carbonate (7.95 g, 58 mmol) was added over 45 minutes. The reaction was sampled after an additional 30 minutes and showed a 68.3% conversion to 4,4'-oxydiphthalic anhydride. The reaction mixture was diluted with 1,2,4-trichlorobenzene (90 g) and filtered. The 4,4'-oxydiphthalic anhydride was allowed to crystallize and was collected, washed with 1,2,4-trichlorobenzene followed by hexane, and dried in an air circulating oven at 120° C. to give crude 4,4'-oxydiphthalic anhydride, 15.6 g (88% yield based on conversion).

EXAMPLE 25

4-Chlorophthalic anhydride (30 g, 160 mmol), tetraphenyl phosphonium bromide (0.3 g, 0.7 mmol), and 2,5-dichlorobenzoic acid (0.08 g, 0.4 mmol) were heated to approximately 220° C. Potassium carbonate (7.95 g, 58 mmol) was added over 45 minutes. The reaction was sampled after addition of the potassium carbonate and showed a 24.9% conversion to 4,4'-oxydiphthalic anhydride. The reaction was heated for an additional 45 minutes. The reaction mixture was diluted with 1,2,4-trichlorobenzene (90 g) and filtered. The 4,4'-oxydiphthalic anhydride was allowed to crystallize and was collected, washed with 1,2,4-trichlorobenzene followed by hexane, and dried in an air circulating oven at 120° C. to give crude 4,4'-oxydiphthalic anhydride, 12.9 g.

EXAMPLE 26

4-Chlorophthalic anhydride (30 g, 16o mmol), tetraphenyl phosphonium bromide (0.3 g, 0.7 mmol), and 2,6-dichlorobenzoic acid (0.08 g, 0.4 mmol) were heated to approximately 220° C. Potassium carbonate (7.95 g, 58 mmol) was added over 45 minutes. The reaction was sampled after addition of the potassium carbonate and showed a 28.3% conversion to 4,4'-oxydiphthalic anhydride. The reaction mixture was diluted with 1,2,4-trichlorobenzene (90 g) and filtered. The 4,4'-oxydiphthalic anhydride was allowed to crystallize and was collected, washed with 1,2,4-trichlorobenzene followed by hexane, and dried in an air circulating oven at 120° C. to give crude 4,4'-oxydiphthalic anhydride, 11.4 g.

EXAMPLE 27

4-Fluorophthalic anhydride (0.44 g, 2.6 mmol shown as FPAN in table below), potassium fluoride (Aldrich, 0.18 g, 3.1 mmol), benzoic acid (Aldrich, 0.28 g, 2.3 mmol shown as BzOH in table below) and dimethyl formamide (Aldrich, 3 ml) were heated in a 160° C. oil bath. The reaction was monitored by GC and showed the following results (BOPAN=benzoyloxyphthalic anhydride; ODPAN=oxydiphthalic anhydride; and HOPAN=hydroxyphthalic anhydride):

| Time | FPAN | GC Area Percent BzOH | BOPAN | ODPAN | HOPAN |
|---|---|---|---|---|---|
| 0.5 hrs. | 10.6 | 10.3 | 37.3 | 17.1 | 0.22 |
| 1.5 hrs. | 3.5 | 5.5 | 57.8 | 19.5 | 1.1 |

EXAMPLE 28

4-Fluorophthalic anhydride (0.44 g, 2.6 mmol shown as FPAN in table below), potassium fluoride (Aldrich, 0.14 g, 2.4 mmol), benzoic acid (Aldrich, 0.31 g, 2.5 mmol shown as BzOH in table below) and N-methyl pyrrolidinone (Aldrich, 3 ml) were heated in a 160° C. oil bath. The reaction was monitored by GC and showed the following results (BOPAN = benzoyloxyphthalic anhydride; ODPAN=oxydiphthalic anhydride; and HOPAN=hydroxyphthalic anhydride):

| Time | FPAN | GC Area Percent BzOH | BOPAN | ODPAN | HOPAN |
|---|---|---|---|---|---|
| 0.5 hrs. | 19.3 | 38.6 | 23.5 | 5.2 | 1.8 |
| 1.5 hrs. | 1.6 | 26.8 | 52.6 | 9.0 | 1.6 |

EXAMPLE 29

3-Fluorophthalic anhydride (19.6 g, 88% pure, 104 mmol), potassium fluoride (7.6 g, 130 mmol), benzoic acid (12.2 g, 100 mmol), and dimethyl formamide (90 g) were heated to 130°–135° C. for 5 hours. An aliquot from the reaction was removed and showed 56% BOPAN and 16% ODPAN (GC area percent). The reaction mixture was filtered and the DMF removed under reduced pressure. Ethyl acetate (17 ml) was added and the suspension filtered to give ODPAN (4.1 g, 92% pure) and a filtrate. The filtrate was allowed to cool to room temperature and the solid removed by filtration, 12.3 g. Analysis of this solid by GC showed the presence of BOPAN (72%) and ODPAN (26%). Hexane was added to the filtrate and a new solid was formed which was collected, 12.2g. GC analysis of this solid showed that it was 60% BOPAN.

EXAMPLE 30

4-Bromophthalic anhydride (BrPAN, 0.53 g, 2.3 mmol), potassium fluoride (0.20 g, 3.4 mmol), benzoic acid (0.32 g, 2.6 mmol), and dimethyl formamide (8.2 g) were heated to about 150° C. The reaction was monitored by GC and showed 5.2 ratio of BrPAN to BOPAN after 2.3 hours.

EXAMPLE 31

4-Chlorophthalic anhydride (ClPAN 0.68 g, 3.7 mmol), benzoic acid (0.43 g, 3.5 mmol), potassium fluoride (0.37 g, 6.4 mmol), and DMF (6.88 g) were heated to about 150° C. The reaction was monitored by GC and showed a 5.4 ratio of CPAN to BOPAN after 4.5 hours.

EXAMPLE 32

3-Bromophthalic anhydride (22.7 g, 100 mmol), potassium benzoate (Aldrich, 17.0 g, 106 mmol), and dimethyl formamide (114 g) were heated to 150° C. The reaction was monitored by GC. After 2.5 hours, GC analysis of the reaction mixture showed a 2.8:1 ratio of 3-benzoyloxyphthalic anhydride to 3-bromophthalic anhydride with smaller amounts of 3-hydroxyphthalic anhydride. The reaction mixture was cooled to 85° C. and the DMF distilled under reduced pressure. Ethyl acetate (90 mls) was added and the reaction vessel heated to reflux. The solids were removed by filtration and the ethyl acetate layer allowed to cool and stand overnight. A slightly off-white solid was collected which contained 3-benzoyloxyphthalic anhydride (76% pure, 12.1 g).

EXAMPLE 33

3-Bromophthalic anhydride (44.4 g, 196 mmol), potassium benzoate (Aldrich, 78.0 g, 487 mmol), and dimethyl formamide (184 g) were heated to 157° C. The reaction was monitored by GC and indicated the presence of 3-hydroxyphthalic anhydride (34 GC area percent), 3-benzoyloxyphthalic anhydride (12.5 GC area percent), and only a small amount of 3-bromophthalic anhydride (2.4 GC area percent).

EXAMPLE 34

4-Chlorophthalic anhydride (10 g, 55 mmol), potassium benzoate (1.0 g, 6.2 mmol) was heated to 162° C. in sulfolane (25 g). Potassium carbonate (3.87 g, 28 mmol) was added and the reaction heated to 175° C. After 4 hours, analysis of the reaction mixture by GC indicated the presence of 4-benzoyloxyphthalic anhydride (10 GC area percent), 4-hydroxyphthalic anhydride (7.7 GC area percent), and 4,4'-oxydiphthalic anhydride (71 GC area percent) along with unreacted 4-chlorophthalic anhydride (11.4 GC area percent).

EXAMPLE 35

4-Chlorophthalic anhydride (10 g, 55 mmol), potassium benzoate (1.0 g, 6.2 mmol) were heated in DMF (25 g) to reflux. Potassium carbonate (3.87 g, 28 mmol) was added. After heating for 7.5 hours, GC analysis of the reaction mixture indicated the presence of unreacted starting material (19.7 GC area percent), 4-benzoyloxyphthalic anhydride (9.6 GC area percent), 4-hydroxyphthalic anhydride (17.0 GC area percent), and 4,4'-oxydiphthalic anhydride (52.9 GC area percent).

EXAMPLE 36

4-Fluorophthalic anhydride (16.7 g, 100 mmol) and sodium benzoate (14.5 g, 101 mmol) were heated to about 145° C. in DMF (70 ml). After heating for 5 hours, the solvent was distilled off under reduced pressure (the temperature was kept at less than 100° C.). Ethyl acetate (50 ml) was added and the suspension refluxed for 30 minutes. The suspension was filtered and the ethyl acetate allowed to cool to give 4-benzoyloxyphthalic anhydride (13.6 g, 86% pure) as a whitish solid. Ethyl acetate (8 mls) was distilled from the mother liquor and hexane added to the hot solution. The solution was allowed to cool and stand for several days upon which a solid benzoyloxyphthalic anhydride precipitated (4.7 g, 79% pure).

EXAMPLE 37

4-Fluorophthalic anhydride (0.40 g, 90% pure), potassium fluoride (0.20 g), and acetic acid (0.14 ml) were heated in DMF (5 ml) at 150° C. for 30 minutes. The reaction mixture was analyzed by gas chromatography-mass spectroscopy (GC-MS) which showed the presence of 4-acetoxyphthalic anhydride (14.8%) and 4-hydroxyphthalic anhydride (9.7%).

EXAMPLE 38

4-Chlorophthalic anhydride (7.5 g, 41.1 mmol) and 1,2,4-trichlorobenzene (Aldrich, 7.5 g) were heated to reflux and dry potassium carbonate (0.55 g, 4.1 mmol) was added. After refluxing for 30 minutes, 4-(3-nitrobenzoyl)oxyphthalic anhydride (0.03 g, 0.1 mmol), tetraphenyl phosphonium bromide (Hokko Chemical, 0.08 g, 0.2 mmol), and potassium carbonate (2.9 g, 21 mmol) were added. The reaction was heated for 7 hours and was then diluted with 1,2,4-trichlorobenzene (50 g), filtered, and the 4,4'-oxydiphthalic anhydride allowed to crystallize. The solid was collected, washed with solvent, and dried in an air circulating oven to give crude 4,4-oxydiphthalic anhydride, 3.9 g (61% isolated yield).

EXAMPLE 39

4-Chlorophthalic anhydride (7.5 g, 41.1 mmol) and 1,2,4-trichlorobenzene (Aldrich, 7.5 g) were heated to reflux and dry potassium carbonate (0.6 g, 4.3 mmol) was added. After refluxing for 30 minutes, 4-benzoyloxyphthalic anhydride (0.024 g, 0.1 mmol), tetraphenyl phosphonium bromide (Hokko Chemical, 0.08 g, 0.2 mmol), and potassium carbonate (2.9 g, 21 mmol) were added. The reaction was heated for 7 hours and was then diluted with 1,2,4-trichlorobenzene (50 g), filtered, and the 4,4'-oxydiphthalic anhydride allowed to crystallize. The solid was collected, washed with solvent, and dried in an air circulating oven to give crude 4,4-oxydiphthalic anhydride, 3.56 g (56% isolated yield).

EXAMPLE 40

4-Chlorophthalic anhydride (7.5 g, 41.1 mmol) and 1,2,4-trichlorobenzene (Aldrich, 7.5 g) were heated to reflux and dry potassium carbonate (0.6 g, 4.3 mmol) was added. After refluxing for 30 minutes, 4-(4-methoxybenzoyl)oxyphthalic anhydride (0.04 g, 0.1 mmol), tetraphenyl phosphonium bromide (Hokko Chemical, 0.08 g, 0.2 mmol), and potassium carbonate (2.84 g, 20.5 mmol) were added. The reaction was heated for 6.5 hours and was then diluted with 1,2,4-trichlorobenzene (30 g), filtered, and the 4,4'-oxydiphthalic anhydride allowed to crystallize. The solid was collected, washed with solvent, and dried in an air circulating oven to give crude 4,4-oxydiphthalic anhydride, 0.62 g (10% isolated yield).

EXAMPLE 41

4-Chlorophthalic anhydride (7.5 g, 41.1 mmol) and 1,2,4-trichlorobenzene (Aldrich, 7.5 g) were heated to reflux and dry potassium carbonate (0.6 g, 4.3 mmol) was added. After refluxing for 30 minutes, 4-(4-methylbenzoyl)oxyphthalic anhydride (0.029 g, 0.10 mmol), tetraphenyl phosphonium bromide (Hokko Chemical, 0.08 g, 0.2 mmol), and potassium carbonate (2.9 g, 21 mmol) were added. The reaction was heated for 10 hours and was then diluted with 1,2,4-trichlorobenzene (30 g), filtered, and the 4,4'-oxydiphthalic anhydride allowed to crystallize. The solid was collected, washed with solvent, and dried in an air circulating oven to give crude 4,4-oxydiphthalic anhydride, 1.53 g (24% isolated yield).

EXAMPLE 42

4-Fluorophthalic anhydride (16.7 g, 100 mmol), 4-(4-chlorobenzoyl)oxyphthalic anhydride (0.32 g, 1.1 mmol), and potassium fluoride (14.4 g, 250 mmol) were suspended in DMF (50 ml) and heated and maintained between 130°-135° C. Water (9 drops) was added after the reaction mixture had been heated for 90 minutes and again after heating for 6 hours. The reaction was monitored by GC and showed a 10% conversion to ODPAN after 4 hours. The reaction mixture was heated for a total of 12 hours. The solvent was distilled under reduced pressure (temperature of less than 100° C.). The residue was treated with 1N potassium hydroxide followed by 40% potassium hydroxide until all solids had dissolved and the pH of the solution was 13. The mixture was then acidified with concentrated hydrochloric acid until the pH of the suspension was 0.8. The suspension was allowed to stir overnight and then the solid was collected, washed, and dried to give 4,4'-oxydiphthalic acid as a white solid, 16.2 g (88% pure).

COMPARATIVE EXAMPLE 1

4-Chlorophthalic anhydride (30 g, 160 mmol) and 1,2,4-trichlorobenzene (60 g) were heated to reflux (approximately 224° C.) and tetraphenyl phosphonium bromide (Hokko Chemical, 0.30 g, 0.7 mmol) was added. Dry potassium carbonate (7.95 g, 58 mmol) was then added in portions over one hour. The reaction was monitored by GC and showed only 2.5% conversion to 4,4'-oxydiphthalic anhydride (ODPAN) 3 hours after addition of carbonate was completed.

COMPARATIVE EXAMPLE 2

4-Chlorophthalic anhydride (7.5 g, 41.1 mmol) and 1,2,4-trichlorobenzene (Aldrich, 7.5 g) were heated to reflux and dry potassium carbonate (0.7 g, 5.1 mmol) was added. After refluxing for 30 minutes, tetraphenyl phosphonium bromide (Hokko Chemical 0.075 g, 0.2 mmol), and potassium carbonate (2.9 g, 21 mmol) were added. The reaction was heated for 22.5 hours and was then diluted with 1,2,4-trichlorobenzene (22 g), filtered, and the 4,4'-oxydiphthalic anhydride allowed to crystallize. The solid was collected, washed with solvent, and dried in an air circulating oven to give crude 4,4-oxydiphthalic anhydride, 0.6 g (10% isolated yield).

COMPARATIVE EXAMPLE 3

4-Chlorophthalic anhydride (CPAN, Occidental Chemical, 31.5 g), potassium benzoate (1.84 g), sodium carbonate (anhydrous from bottle, but not dried further, 12 g), and N-methyl-2-pyrrolidinone (NMP, previously opened "anhydrous" reagent, 20 g) were heated. At 85° C., the reaction mixture became gelatinous. The reaction mixture was then heated to 140° C. GC analysis of the reactor contents showed only 3.3% CPAN at 85° C. and 1.6% at 140° C. No ODPA was seen by GC analysis.

COMPARATIVE EXAMPLE 4

4-Chlorophthalic anhydride (CPAN, Occidental Chemical, 31.5 g), potassium benzoate (1.84 g), potassium carbonate (anhydrous from bottle, but not dried further, 13.6 g), 18-crown-6 (trace as internal standard), and N-methyl-2-pyrrolidinone (NMP, previously opened "anhydrous" reagent, 20 g) were heated. At 95° C., the reaction mixture became gelatinous. The reaction mixture was heated at 200° C. for thirty minutes and sampled and analyzed by GC. The initial reaction mixture consisted of 51% CPAN. The reaction mixture at 95° C. contained 25% CPAN and the reaction mixture at 200° C. contained 12% CPAN. No trace of ODPA formation was evident by GC analysis.

We claim:

1. A process for the preparation of oxydiphthalic anhydride and acyloxyphthalic anhydrides comprising reacting, in a substantially anhydrous medium, a halophthalic anhydride with an alkali metal salt selected from the group consisting of potassium carbonate and sodium carbonate in the presence of at least a catalytically effective amount of a carboxylic acid or acid derivative, where said carboxylic acid or acid derivative does not contain a substituent that interferes with said reaction.

2. A process according to claim 1 wherein said carboxylic acid or acid derivative is selected from the group consisting of benzoic acid, substituted benzoic acids, benzoic acid salts, salts of substituted benzoic acids, hydrolyzable benzoyl esters, hydrolyzable substituted benzoyl esters, $C_2$ to $C_{12}$ straight, branched, and cyclic alkyl carboxylic acids, hydrolyzable esters of said alkyl carboxylic acids, and salts of said alkyl carboxylic acids.

3. A process according to claim 2 wherein said carboxylic acid or acid derivative is selected from the group consisting of benzoic acid, benzoic acids salts, substituted benzoic acids, and salts of substituted benzoic acids.

4. A process according to claim 2 wherein said carboxylic acid or acid derivative is selected from the group consisting of hydrolyzable benzoyl esters, and hydrolyzable substituted benzoyl esters.

5. A process according to claim 2 wherein said carboxylic acid or acid derivative is selected from the group consisting of alkyl carboxylic acids, hydrolyzable esters of alkyl carboxylic acids, and salts of alkyl carboxylic acids.

6. A process according to claim 1 wherein the process is conducted in an aprotic solvent.

7. A process according to claim 6 wherein said solvent is selected from a group consisting of dimethyl formamide, N-methyl pyrrolidone, dimethyl acetamide, hexamethylphosphoramide dimethyl sulfoxide, sulfolane, and dimethyl sulfone chlorobenzene, dichlorobenzene, trichlorobenzene, and benzonitrile.

8. A process according to claim 1 wherein said carboxylic acid or acid derivative is a Li, Na, K, Cs, or $NH_4^+$ salt of benzoic acid or of a substituted benzoic acid.

9. A process according to claim 6 wherein said solvent is non-polar and said reaction is conducted in the presence of a phase transfer catalyst.

10. A process according to claim 9 wherein said phase transfer catalyst is selected from the group consisting of tetraphenyl phosphonium benzoates, tetraphenyl phosphonium substituted benzoates, and tetraphenyl phosphonium halides.

11. A process for the preparation of oxydiphthalic anhydride and acyloxyphthalic anhydrides comprising reacting a halophthalic anhydride with an alkali metal salt selected from the group consisting of potassium fluoride and cesium fluoride in the presence of at least a catalytically effective amount of a carboxylic acid or acid derivative, where said carboxylic acid or acid derivative does not contain a substituent that interferes with said reaction.

12. A process according to claim 11 wherein said carboxylic acid or acid derivative is selected from the group consisting of benzoic acid, substituted benzoic acids, benzoic acid salts, salts of substituted benzoic acids, hydrolyzable benzoyl esters, hydrolyzable substituted benzoyl esters, $C_2$ to $C_{12}$ straight, branched, and cyclic alkyl carboxylic acids, hydrolyzable esters of said alkyl carboxylic acids, and salts of said alkyl carboxylic acids.

13. A process according to claim 12 wherein said carboxylic acid or acid derivative is selected from the group consisting of benzoic acid, benzoic acids salts, substituted benzoic acids, and salts of substituted benzoic acids.

14. A process according to claim 12 wherein said carboxylic acid or acid derivative is selected from the group consisting of hydrolyzable benzoyl esters, and hydrolyzable substituted benzoyl esters.

15. A process according to claim 12 wherein said carboxylic acid or acid derivative is selected from the group consisting of alkyl carboxylic acids, hydrolyzable esters of alkyl carboxylic acids, and salts of alkyl carboxylic acids.

16. A process according to claim 11 wherein the process is conducted in an aprotic solvent.

17. A process according to claim 16 wherein said solvent is selected from a group consisting of dimethyl formamide, N-methyl pyrrolidone, dimethyl acetamide, hexamethylphosphoramide, dimethyl sulfoxide, sulfolane, dimethyl sulfone, chlorobenzene, dichlorobenzene, trichlorobenzene, and benzonitrile.

18. A process according to claim 11 wherein said carboxylic acid or acid derivative is a Li, Na, K, Cs, or $NH_4^+$ salt of benzoic acid or of a substituted benzoic acid.

19. A process according to claim 16 wherein said solvent is a non-polar solvent and said reaction is conducted in the presence of a phase transfer catalyst.

20. A process according to claim 19 wherein said phase transfer catalyst is selected from the group consisting of tetraphenyl phosphonium benzoates, tetraphenyl phosphonium substituted benzoates, and tetraphenyl phosphonium halides.

21. A process according to claim 11 wherein the product is predominantly an acyloxyphthalic anhydride, and wherein said carboxylic acid or acid derivative is a reactant.

22. A process for the preparation of a product that is predominantly an acyloxyphthalic anhydride comprising reacting an halophthalic anhydride with an alkali metal salt selected from the group consisting of potassium carbonate and sodium carbonate in the presence of a carboxylic acid or acid derivative, where said acid or acid derivative does not contain a substituent that interferes with said reaction.

23. An acyloxyphthalic anhydride of the formula

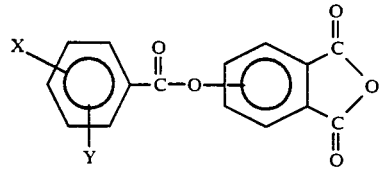

where X and Y are substituents independently selected from the group consisting of H, F, Cl, Br, $NO_2$, $CH_3$, $CF_3$, $CCl_3$ and CN, provided that X and Y may not both be H.

24. An acyloxyphthalic anhydride according to claim 23 namely 3-(4-chlorobenzoyloxy)phthalic anhydride.

25. An acyloxyphthalic anhydride according to claim 23 namely 4-(4-chlorobenzoyloxy)phthalic anhydride.

26. An acyloxyphthalic anhydride according to claim 23 namely 4-(3-chlorobenzoyloxy)phthalic anhydride.

27. An acyloxyphthalic anhydride according to claim 23 namely 4-(2-chlorobenzoyloxy)phthalic anhydride.

28. An acyloxyphthalic anhydride according to claim 23 namely 4-(3-bromobenzoyloxy)phthalic anhydride.

29. An acyloxyphthalic anhydride according to claim 23 namely 4-(2,4-dichlorobenzoyloxy)phthalic anhydride.

30. An acyloxyphthalic anhydride according to claim 23 namely 4-(2,5-dichlorobenzoyloxy)phthalic anhydride.

31. An acyloxyphthalic anhydride according to claim 23 namely 4-(2,6-dichlorobenzoyloxy)phthalic anhydride.

32. An acyloxyphthalic anhydride according to claim 23 namely 4-(3,4-dichlorobenzoyloxy)phthalic anhydride.

33. An acyloxyphthalic anhydride according to claim 23 namely 4-(3,5-dichlorobenzoyloxy)phthalic anhydride.

34. An acyloxyphthalic anhydride according to claim 23 namely 4-(3-methoxybenzoyloxy)phthalic anhydride.

35. An acyloxyphthalic anhydride according to claim 23 namely 4-(4-methylbenzoyloxy)phthalic anhydride.

36. An acyloxyphthalic anhydride according to claim 23 namely 4-(3-nitrobenzoyloxy)phthalic anhydride.

37. An acyloxyphthalic anhydride according to claim 23 namely 4-(4-nitrobenzoyloxy)phthalic anhydride.

38. An acyloxyphthalic anhydride according to claim 23 namely 4-(2-(trifluoromethyl)benzoyloxy)phthalic anhydride.

39. An acyloxyphthalic anhydride according to claim 23 namely 4-(3-(trifluoromethyl)benzoyloxy)phthalic anhydride.

40. An acyloxyphthalic anhydride according to claim 23 namely 4-(4-(trifluoromethyl)benzoyloxy)phthalic anhydride.

41. An acyloxyphthalic anhydride of the formula:

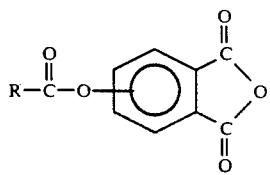

where R is selected from the group consisting of $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, and $C_{11}H_{23}$, including branched isomers of those formulas and cyclic saturated hydrocarbon radicals containing 3 to 11 carbon atoms.

42. An acyloxyphthalic anhydride according to claim 41 wherein R is $C_2H_5$.

43. A process according to claim 1 wherein no solvent is present during said reaction.

44. A process according to claim 1 wherein said process is conducted at a temperature of about 120° to 275° C.

45. A process according to claim 11 wherein said process is conducted at a temperature of about 120° to 275° C.

46. A method of making oxydiphthalic anhydride comprising
(A) preparing a composition by mixing together
  (1) a halophthalic anhydride;
  (2) a basic alkali metal salt; and
  (3) a catalyst selected from the group consisting of benzoic acid, substituted benzoic acids, benzoic acid salts, substituted benzoic acid salts, hydrolyzable benzoyl esters, hydrolyzable substituted benzoyl esters, $C_2$ to $C_{12}$ straight, branched, and cyclic alkyl carboxylic acids, hydrolyzable esters of said alkyl carboxylic acids, and salts of said alkyl carboxylic acids; and
(B) maintaining the total moisture content of said composition at less than 2000 ppm while reacting said composition at a temperature of about 120° to about 275° C., where said catalyst does not contain a substituent that interferes with said reaction.

47. A method according to claim 46 wherein said reaction is solventless.

48. A method according to claim 46 wherein an aprotic solvent is present during said reaction.

49. A method according to claim 48 wherein said basic alkali metal salt is potassium carbonate and said solvent contains about 0.05 to about 0.5 mole % total water, based on said halophthalic anhydride.

50. A method according to claim 49 wherein said aprotic solvent is non-polar and said catalyst is selected from the group consisting of nitrobenzoic acid, dinitrobenzoic acid, halobenzoic acids, dihalobenzoic acids, trihalobenzoic acids, cyanobenzoic acids, and trihalomethyl benzoic acids.

51. A method according to claim 48 wherein said aprotic solvent is polar and said catalyst is selected from the group consisting of benzoic acid, alkylbenzoic acids, alkoxybenzoic acids, and salts thereof.

52. A process for preparing oxydiphthalic anhydride comprising reacting, in 1,2-dichlorobenzene, 3-chlorophthalic anhydride or 4-chlorophthalic anhydride with potassium carbonate or sodium carbonate in the presence of a phase transfer catalyst and an added catalyst selected from the group consisting of 3-chlorobenzoic acid, 4-chlorobenzoic acid, salts of 3-chlorobenzoic acid, salts of 4-chlorobenzoic acid, and mixtures thereof.

* * * * *